United States Patent
Bernard

(10) Patent No.: US 8,734,510 B2
(45) Date of Patent: May 27, 2014

(54) INTRAOCULAR LENS FOR CAPSULAR BAG

(75) Inventor: Pascal Bernard, Nieul sur Mer (FR)

(73) Assignee: Carl Zeiss Meditec SAS, Perigny (FR)

( * ) Notice: Subject to any disclaimer, the term of this patent is extended or adjusted under 35 U.S.C. 154(b) by 312 days.

(21) Appl. No.: 12/738,480

(22) PCT Filed: Oct. 15, 2008

(86) PCT No.: PCT/FR2008/001447
§ 371 (c)(1),
(2), (4) Date: Apr. 16, 2010

(87) PCT Pub. No.: WO2009/087302
PCT Pub. Date: Jul. 16, 2009

(65) Prior Publication Data
US 2010/0222879 A1      Sep. 2, 2010

(30) Foreign Application Priority Data
Oct. 16, 2007 (FR) ...................................... 07 58366

(51) Int. Cl.
*A61F 2/16* (2006.01)

(52) U.S. Cl.
CPC ................. *A61F 2/16* (2013.01); *A61F 2/1613* (2013.01); *A61F 2002/1681* (2013.01)
USPC .......... 623/6.16; 623/6.46; 623/6.49

(58) Field of Classification Search
CPC .. A61F 2/16; A61F 2/1613; A61F 2002/1681
USPC ............... 623/6.16, 6.46, 6.49, 6.17
See application file for complete search history.

(56) References Cited

U.S. PATENT DOCUMENTS

| 5,549,670 | A * | 8/1996 | Young et al. ............... 623/6.16 |
| 6,926,744 | B1 | 8/2005 | Bos et al. |
| 2004/0042073 | A1 | 3/2004 | Pynson |
| 2005/0107874 | A1 | 5/2005 | Assia |
| 2005/0187621 | A1 | 8/2005 | Brady |
| 2006/0142855 | A1 | 6/2006 | Vaudant et al. |

FOREIGN PATENT DOCUMENTS

| FR | 2 795 944 A1 | 1/2001 |
| WO | 00/66041 A1 | 11/2000 |
| WO | 01/03610 A1 | 1/2001 |

(Continued)

OTHER PUBLICATIONS

International Search Report, dated Aug. 6, 2009, from corresponding PCT application.

*Primary Examiner* — David H Willse
*Assistant Examiner* — Javier Blanco
(74) *Attorney, Agent, or Firm* — Young & Thompson

(57) ABSTRACT

An intraocular lens to be implanted into the capsular bag after ablation of the crystalline lens includes a central optical portion and a haptic portion including haptic members arranged on the periphery of the optical part and for positioning the intraocular lens in the capsular bag. On the one hand, the posterior surface of the optical portion includes a sharp ridge at the peripheral edge and, on the other hand, the posterior surface of the haptic members includes a proximal area in the vicinity of the peripheral edge of the optical portion, each proximal area including at least one tooth extending substantially along the entire width of each haptic member, the tooth or teeth having a sharp edge that becomes serrated in the posterior capsule in order to limit the migration of the epithelial cells of the haptic members towards the optical portion.

16 Claims, 3 Drawing Sheets

(56) References Cited

FOREIGN PATENT DOCUMENTS

| WO | 03/037225 A1 | 5/2003 |
| WO | 03/039409 A1 | 5/2003 |
| WO | 2005/032427 A1 | 4/2005 |
| WO | 2005/055875 A2 | 6/2005 |
| WO | WO 2006123428 A1 * | 11/2006 |

* cited by examiner

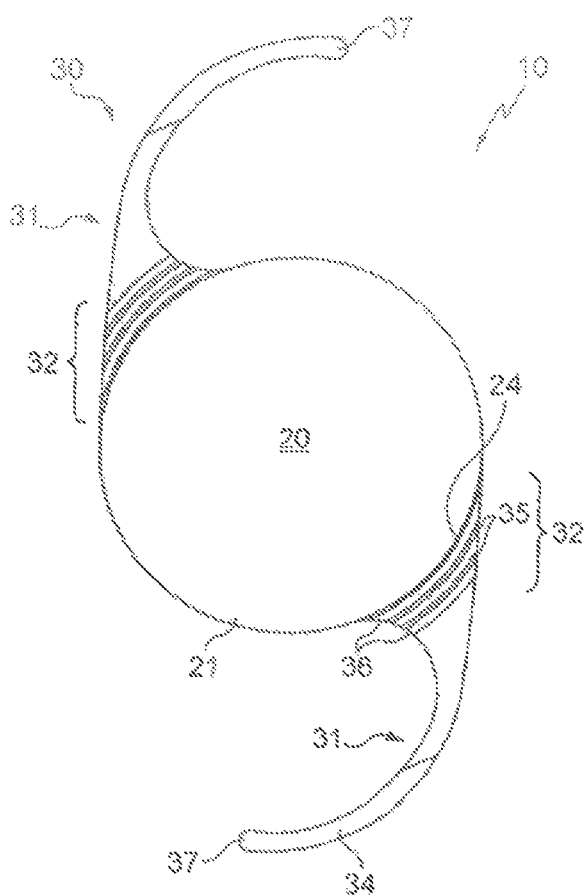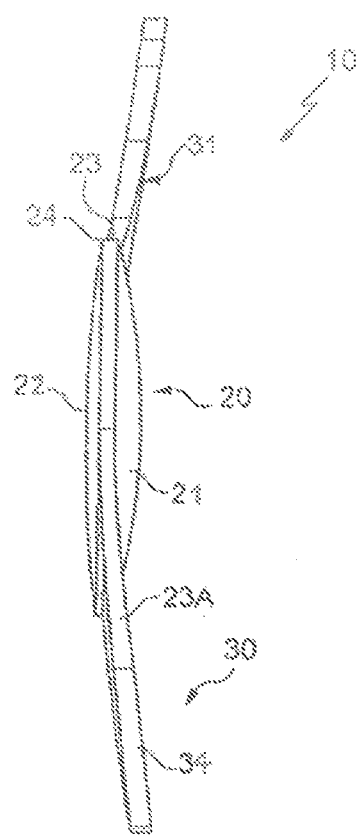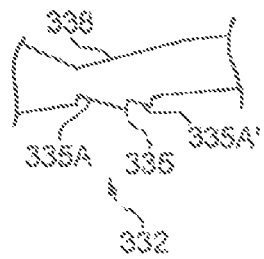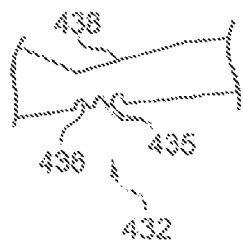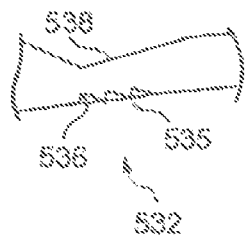

INTRAOCULAR LENS FOR CAPSULAR BAG

BACKGROUND OF THE INVENTION

1. Field of the Invention

The present invention relates to intraocular lenses or implants designed to be implanted in the capsular sac after the ablation of the crystalline lens suffering from cataract.

2. Description of the Related Art

The ablation of the crystalline lens is most frequently carried out by capsulotomy of the leaf or anterior capsule followed by a phacoemulsification of the crystalline lens and the cleaning of the site and notably the capsular sac in order to eliminate the epithelial cells. However, Elschnig pearls that form from the germinative cells subsist on the equator of the capsular sac after the surgical operation. These cells migrate along the posterior capsule and cause the opacification of the posterior capsule. Because of the opacification of the posterior capsule, also called second cataract, in the three years following the ablation of the crystalline lens and the implantation of an intraocular lens, approximately thirty per cent of patients need a new operation, namely a capsulotomy of the posterior capsule by Nd:YAG laser, with the disadvantage of the creation of communication between the anterior and posterior segments of the eye. Moreover, the opacification of the posterior capsule (PCO) forms the most common complication in cataract surgery.

In general, the intraocular lens comprises an optic portion which provides the optic and notably refractive correction and a haptic portion comprising at least one haptic element and in practice at least two haptic elements which rest in the equatorial zone of the capsular sac, and even the ciliary sulcus, and ensure the positioning of the optic axis of the optic portion substantially coinciding with the optic axis of the eye and of the pupil. When the haptic elements are angled anteriorly, the optic portion is in contact with the posterior capsule.

In a study by Nagata et al. "Optic sharp edge or convexity: comparison of effect on posterior capsular opacification", Jpn J Opthalmol., Vol. 40; 397-402, 1996, they found that a rounded edge of the posterior face of the optic allows the invasion of the epithelial cells behind the optic while a sharp edge, also called "square" edge, is effective in reducing the opacification of the posterior capsule. In the article "Posterior capsule opacification" by Nishi, J Cataract Refract Surg— Vol. 25, January 1999, the author confirmed that the sharp or square edge of an optic produces a "discontinuity or a sharp bend" in the posterior capsule which is associated with a reduced incidence of opacification of the posterior capsule.

Square-edged intraocular lenses, also called anti-PCO intraocular lenses, currently exist in two types. On the one hand, there are three-part intraocular lenses comprising an optic portion, for example made of flexible material such as an acrylic polymer, and two haptic elements made of polypropylene or another rigid material anchored in the periphery of the optic portion, and, on the other hand, there are intraocular lenses made in one piece and of flexible material or a combination of rigid and flexible material.

In an article entitled "Evaluation of lens epithelial cell migration in vivo at the haptic-optic junction of a one-piece hydrophobic acrylic intraocular lens", Nixon and Apple report the much higher frequency of opacification of the posterior capsule requiring a capsulotomy with the intraocular lenses in one part made of acrylic compared with those with intraocular lenses in three parts comprising an optic made of acrylic and fitted haptic elements made of polypropylene. One of the problems with one-piece intraocular lenses reported by these authors is the absence of an effective square or sharp edge at the junction of the posterior face of the optic with the posterior face of the haptic elements. The authors recommend a sharp or square edge of 360° on the posterior face of the optic.

It has also been found that the migration of the epithelial cells is preferably carried out by means of the haptic elements. Specifically, during the capsular symphysis, that is to say in the weeks and months following the implantation of the intraocular lens, the leaves of the sac come together at the haptics and the periphery of the optic, trapping the epithelial cells in zones located essentially at the haptic elements of the implant. These cells then migrate toward the centre of the optic following an axial offset between the optic and the haptic elements.

Also known is document WO 01/03610 which describes an intraocular lens made in one piece of rigid material such as PMMA, or of a hydrophobic or hydrophilic flexible material and notably silicone, the acrylic polymers, and even polyHEMA, the haptic portion of which makes an angle of between 5° and 12° directed toward the anterior face, a zone of connection between the optic portion and the haptic elements, a radial extension of the connection zone of which the posterior face is placed on the spherical cap of the posterior face of the optic portion and a step made by an axial offset between the posterior face of the optic portion and the connection zone of the optic element.

But, with such a geometry, the posterior face of the haptic elements cannot be in the continuity of the posterior face of the optic but is necessarily axially offset toward the front.

Also known is document WO 03/039409 which describes an intraocular lens in one piece or several pieces made of a flexible or rigid material in which the periphery of the optic portion comprises two or three steps from the periphery of the posterior face of the optic portion, in which each of these steps forms a sharp or square edge designed to prevent the migration of the epithelial cells behind the optic portion.

Such a geometry does not provide a solution to the problem of migration at the junction between the haptic elements and the optic portion when the lens is made in a single piece. Similarly, the formation of the plurality of steps in the cylindrical periphery of the optic portion cannot provide a good contact with the posterior capsule in order to form an effective barrier against the progression of the epithelial cells between the posterior face of the optic portion and the posterior capsule.

Finally, document WO 2005/055875 is known in which is described an intraocular lens for implantation into the capsular sac, comprising an optic portion and a haptic portion, the posterior face of the optic portion having a sharp ridge on the peripheral edge and the posterior face of the haptic elements comprising at least one tooth. However, the sharp ridge on the peripheral edge is interrupted at the junction of the haptic and optic elements.

SUMMARY OF THE INVENTION

The object of the present invention is to improve or eliminate the aforementioned drawbacks of anti-PCO lenses.

According to the invention, an intraocular lens is provided for implantation in the capsular sac after ablation of the crystalline lens, comprising a central optic portion and a haptic portion comprising haptic elements arranged on the periphery of the optic portion in order to position the intraocular lens in the capsular sac, the intraocular lens being characterized in that, on the one hand, the posterior face of the optic portion has a sharp ridge on the peripheral edge, and, on the other hand, the posterior face of the haptic elements comprises a proximal zone close to the peripheral edge of the optic portion, each proximal zone comprising at least one tooth extending over substantially the whole width of each haptic element, the tooth or teeth having a sharp edge designed to indent itself into the posterior capsule in order to limit the migration of the epithelial cells of the haptic elements toward the optic portion.

Thus, the intraocular lens of the present invention comprises, at the junction of the haptic and optic elements, at least two anti-PCO barriers, the first being defined by the sharp ridge of the peripheral edge at the junction of the haptic and optic elements, and the second defined by the tooth or teeth on the posterior surface of the haptic elements.

Such an intraocular lens may also comprise one or more of the following features:

Thus, the proximal zone may comprise a network of teeth of at least two parallel teeth.

Thus, the sharp ridge of the tooth or teeth of each haptic element is in continuity with the curvature of the posterior surface of the haptic element concerned.

Thus, the radial section of the teeth of each haptic element may have substantially the same configuration and the same dimensions.

Thus, the sharp edge of each tooth of each haptic element may be substantially parallel to the sharp ridge of the peripheral edge of the optic portion and may be placed on a surface slightly offset relative to the posterior face of the optic portion by the height of the sharp ridge at the peripheral edge of the optic.

Thus, the sharp ridge of the tooth or teeth may be defined at the intersection of an outer slope at an acute angle relative to the posterior surface of the haptic element and an inner slope substantially perpendicular to the posterior surface of the haptic element.

Thus, the height of each tooth may be between 0.05 mm and 0.1 mm approximately.

Thus, the sharp ridges of the teeth may be at the intersection of two inclined slopes forming an angle of between 40° and 70°.

Thus, the grooves between the successive teeth of a network of teeth may have a radial section in the shape of a U or of a V, and the sharp ridges may be defined at the intersection of the posterior surface of the haptic element concerned and the free edge of the grooves.

Thus, the tooth or teeth may define a sharp ridge slightly protruding relative to the posterior surface of the haptic element concerned, or in continuity therewith.

Thus, the tooth or teeth of a network of teeth on the posterior surface of the haptic element concerned may have different radial widths.

Thus, the tooth or teeth on the posterior surface of the haptic element concerned may comprise a slope inclined both posteriorly and toward the outer periphery of the optic portion.

Thus, the tooth or teeth of each haptic element may extend over a radial width of 0.5 to 0.8 mm.

Thus, the tooth or teeth of each haptic element concerned may extend in a widened proximal zone of the haptic element of generally triangular shape between the peripheral edge of the optic portion and the opposite lateral edges of the haptic element concerned.

Thus, the posterior surface of the haptic elements may be slightly offset relative to the spherical posterior surface of the optic portion by the height of the sharp ridge at the peripheral edge.

Thus, the intraocular lens may be mainly or entirely made of a hydrophobic or hydrophilic flexible acrylic polymer.

Other features and advantages of the invention will also become apparent in the following description.

BRIEF DESCRIPTION OF THE DRAWING FIGURES

In the appended drawings, given as nonlimiting examples:

FIG. 1 is a view of the posterior face of an intraocular lens of a first embodiment of the invention;

FIG. 2 is a view in elevation of the intraocular lens of the first embodiment;

FIG. 9 is an enlarged detail view to illustrate the network of teeth of one of the haptic elements according to another embodiment;

FIG. 10 is an enlarged detail view to illustrate the network of teeth of one of the haptic elements according to another embodiment;

FIG. 11 is an enlarged detail view to illustrate the network of teeth of one of the haptic elements according to another embodiment.

DETAILED DESCRIPTION OF THE INVENTION

Figure 3:
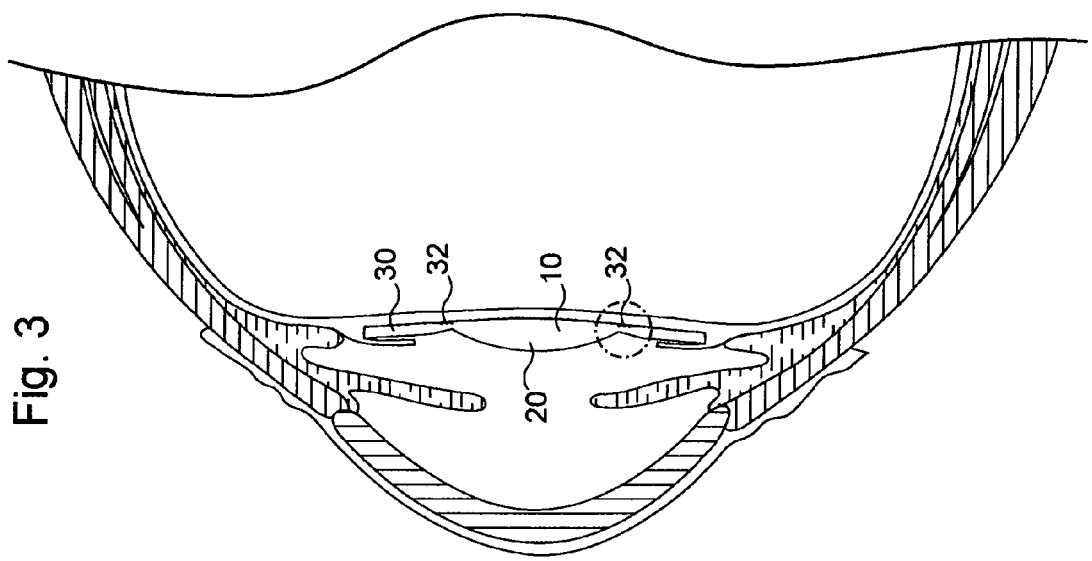
FIG. 3 is an axial section of an eye after ablation of the crystalline lens and the implantation of the intraocular lens of the first embodiment.
Figure 4:
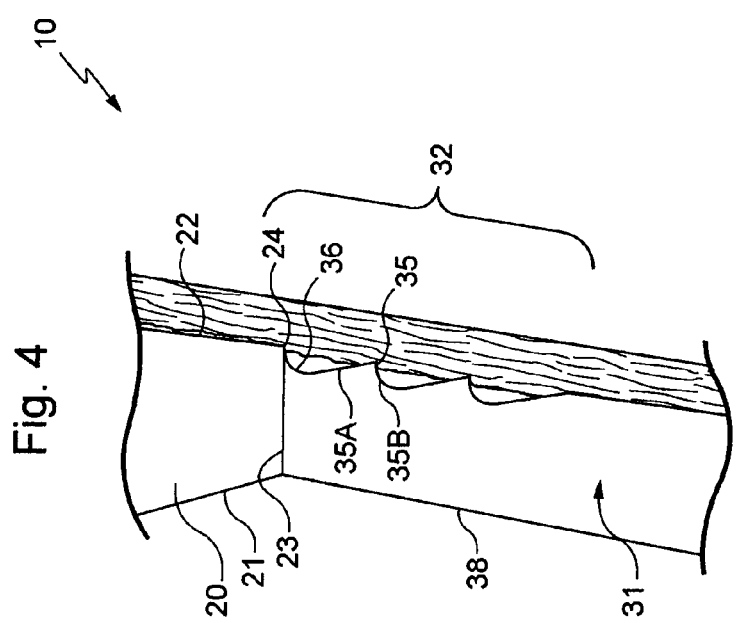
FIG. 4 is an enlarged detail view of the encircled zone of FIG. 3 to illustrate the contact of the posterior surface of the optic and of one of the haptic elements with the posterior capsule of the capsular sac.

The first embodiment of an intraocular lens will be described with reference to FIGS. 1 to 4. The intraocular lens 10 comprises an optic or optic portion 20 and a haptic portion 30. This intraocular lens 10 is preferably made in one piece by machining in flexible transparent and biocompatible material such as acrylic polymer, polyHEMA, silicone preferably in hydrophobic flexible material, notably a hydrophobic acrylic polymer. However, such a lens may comprise one or more zones of rigid material, for example by the use of the "Flexi-zone" technology described in document EP 1 003 446.

The optic portion 20 forms the central portion of the intraocular lens 10 and has a circular contour. The curvature of the anterior and posterior faces 20 determine the notably refractive correction in substitution of the excised crystalline lens. The anterior face 21 and/or the posterior face 22 may be spherical and/or aspherical. The radius of curvature of the spherical posterior face is preferably constant irrespective of the curvature of the anterior face of the optic portion. In this case, it is the curvature of the anterior face that may be spherical or aspherical, the radius or radii of curvature conforming to the correction chosen by the surgeon in order to satisfy the desiderata of the patient. The peripheral edge 23 of the optic portion has a cylindrical shape, or is slightly frusto-conical tapering off anteriorly, as illustrated. The intersection of this peripheral edge 23 and the posterior face 22 of the optic portion 20 forms a sharp ridge 24 also called a square edge or sharp edge. The angle between the peripheral edge 23 and the posterior face 22 is preferably between 80° and 100°. The intersection of the peripheral edge 23 and the anterior face 21 of the optic portion 20 may be sharp or rounded.

The haptic portion 30 comprises at least two haptic elements. As illustrated, the haptic portion 30 comprises two haptic elements 31. These haptic elements 31, as illustrated, form open arches 31, 32, in the various embodiments of the present application, or if necessary closed arches, or even "flat" haptic elements, which may have holes in them. Each arch is preferably the mirror image of the other about a diameter of the optic portion 20. These arches, as illustrated, are generally C-shaped or J-shaped, with a proximal zone 32 close to the optic portion 20 and which in practice forms the zone of connection with the haptic portion. The circumferential extent of the proximal zone at the junction with the optic portion is widened and relatively large, for example at an angle of 40° to 80° and preferably from 45° to 60° from the periphery of the optic portion 20 as illustrated. The proximal zone or portion 32 of each haptic element 31 has a generally triangular shape, from the junction with the optic portion 20 extending generally radially outward from the zone of connection with the optic portion. The distal portion 34 of each haptic element 31 has a relatively uniform width and terminates in a rounded free end 37 which may if necessary be widened relative to the width of the rest of the distal portion. The width of the distal portion 34 of the haptic element 31 is preferably of the order of 0.30 to 0.60 mm and the measured thickness, parallel to the axis of the optic, of the order of 0.30 to 0.60 mm.

According to the present invention, the posterior face of the proximal portion 32 of each haptic element 31 comprises at least one tooth and preferably a plurality or network of teeth 35 that are substantially parallel and radially spaced from one another. These teeth 35 form as many individual barriers to the migration of the epithelial cells toward the periphery of the posterior face 22 of the optic portion 20 and between them grooves 36 are formed that are capable of trapping epithelial cells which have been able to pass through the barrier formed by the tooth 35 which is just on the outside of the groove.

Preferably, the teeth 35 extend circumferentially between the lateral—more or less radial—opposite and respectively concave and convex edges of the proximal portion 32 of the haptic element 31 concerned. As illustrated, these teeth 35 extend over arcs of a circle parallel to the peripheral circular edge 23 of the optic portion and therefore concentric with the latter. The radial distance between the respective teeth and therefore the width of the grooves between them is from 0.1 mm to 0.3 mm approximately. In this first embodiment, the radial distance that separates the ridge of the first tooth from the ridge of the peripheral edge 23 of the posterior face 22 of the optic portion 20 is equal to the distance between the successive teeth 35.

In the first embodiment, there are two teeth 35 and three grooves 36, respectively between the peripheral edge 23 of the posterior face 22 of the optic portion 20 and the first tooth 35, between the first and second tooth 35, and beyond this second tooth 35. The proximal portion 32 of the haptic element 31 may comprise, over all or part of its radial extent, at least one tooth, and preferably a network or a plurality of teeth, and in practice a maximum of five teeth.

In this embodiment, the network of teeth has a "sawtooth" shape. Each tooth 35 comprises an inner slope 35A inclined anteriorly at an angle of approximately 40° to 70° and an outer slope 35B substantially parallel to the axis of the optic portion 20 and perpendicular to the posterior surface of the distal portion of the haptic element. The outer slope 35B of the second tooth is extended by a slope parallel to the inner slope 35A of the first tooth and which joins the posterior face of the proximal portion 32 of the haptic element 31.

In this first embodiment, the anterior face 38 of the proximal portion 32 of the haptic element 31 is very slightly tapered toward the peripheral edge 24 of the optic portion so that the thickness of the haptic element 31 in the proximal portion 32 is almost constant.

As illustrated in FIG. 1, the direction of the curvature of the haptic elements 31 is counterclockwise. Evidently the direction of the curvature of the haptic elements may be the opposite direction. As illustrated, the terminal end 37 of each haptic element 31 is on the extension of one and the same diameter of the optic portion 20. But the circumferential extent of the distal portion 34 may be greater or lesser.

Such an intraocular lens may be implanted by means of a surgical tweezer or preferably by means of a cassette injector as described in document EP 1 453 440. In the case of the injection of an intraocular lens made of hydrophobic acrylic, the intraocular lens will be sterilized in its cassette by exposure to ethylene oxide gas, by gamma radiation, or by hydrogen peroxide plasma sterilization.

The radius of the spherical curvature of the posterior face 22 of the optic portion 20 and the haptic portion 31 ensures, after the post-operative retraction of the capsular bag or sac, an intimate contact between the posterior face 22 of the intraocular lens 10 and a posterior capsule of the capsular bag or sac, and more particularly at the peripheral edge 34 of the optic portion 20 and at the network of teeth 35. The anterior angulation of the haptic elements 31 (see FIG. 2) produces an axial pressure force at the sharp ridge 24 of the peripheral edge 23 and of the network of teeth 35 sufficient to produce a slight indentation of the sharp ridge of the teeth and/or the sharp ridge of the peripheral edge in the tissue of the posterior capsule (see FIG. 4) and hence in principle three levels of effective barriers against the migration of the epithelial cells.

The intraocular lens 110 of the second embodiment comprises most of the features of the first embodiment. The same elements or the elements having the same functions are designated by the same reference numbers increased by 100. Only the modified features of the second embodiment will be described.

Figure 5:
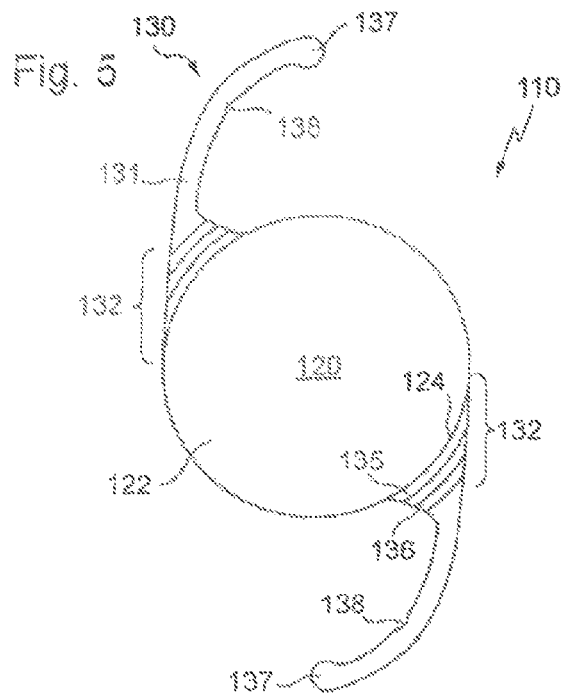
FIG. 5 is a view of the posterior face of an intraocular lens of a second embodiment of the invention.
Figure 6:
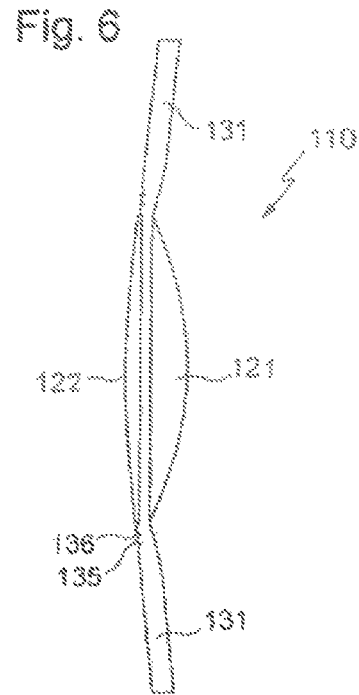
FIG. 6 is a view in elevation of the intraocular lens of the second embodiment.
Figure 7:
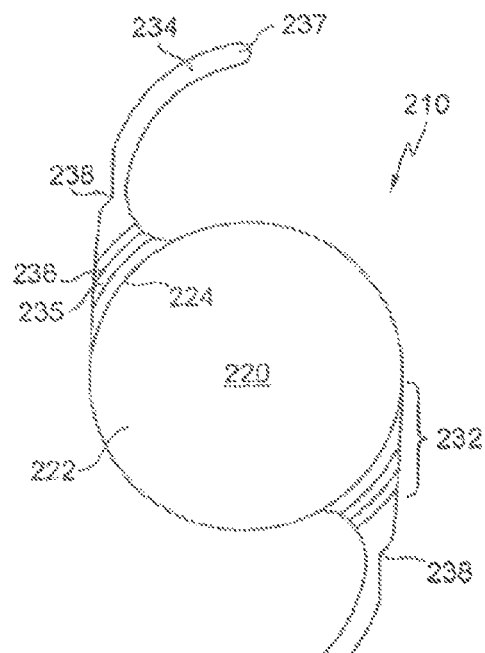
FIG. 7 is a view of the posterior face of an intraocular lens of a third embodiment of the invention.

The second embodiment illustrated in FIGS. 5 and 6 has essentially two differences relative to the first embodiment. The first difference is the shape of the arches that are formed by the haptic elements 131 of the haptic portion 130 but that is still C-shaped or J-shaped. The proximal zone or portion 132 between the haptic elements 131 has a smaller circumferential extent, from 50° to 60° approximately. Moreover, the concave edge of the proximal portion 132 is virtually rectilinear, thus accentuating the triangular shape of the proximal portion when the lens is seen from the front. Then the distal portion 134 of the haptic elements 131 is less curved. Similarly, the free end 137 of each haptic element 131 comprises a rounded shape the width of which is greater than the width of the rest of the distal portion 134 of the haptic element 131. Such a haptic configuration has the advantage of allowing the rectilinear lengthening of the haptic element in order to facilitate the injection of the "leading" arch. Finally, a notch 138 is formed on the concave edge of the distal portion 134.

The intraocular lens 210 of the second embodiment comprises most of the features of the first embodiment. The same elements or the elements having the same functions are designated by the same reference numbers increased by 200. Only the modified features of the third embodiment will be described.

Figure 8:
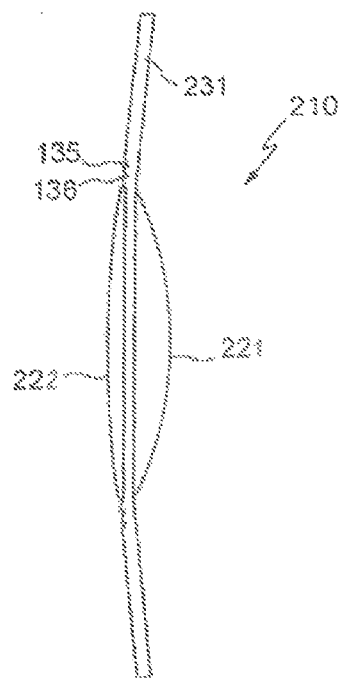
FIG. 8 is a view in elevation of the intraocular lens of the third embodiment.

The shape and general curvature of the C-shaped or J-shaped arches formed by the haptic elements 231 of the haptic portions 230 of the third embodiment, illustrated in FIGS. 8 and 9, are similar to those of the second embodiment. But instead of a half-way notch on the concave edge of the distal portion of the haptic elements 231, in the third embodiment, a deeper notch 238 is present on the convex edge of the haptic elements 231 just beyond the proximal portion 232 of the haptic elements 231.

The production, insertion and implantation and the barrier effect of the square peripheral edge of the optic portion and the network of teeth of the proximal portion of the haptic elements after the retraction of the capsular sac of such an intraocular lens according to the second or third embodiment are substantially the same as those of the first embodiment.

FIGS. 9 to 11 represent variants of the network of teeth capable of being incorporated into the intraocular lenses in such an anti-PCO intraocular lens and notably that of the first, second and third embodiments.

Unlike the first three embodiments in which the thickness of the proximal portion of the haptic elements is substantially uniform, that of the variants of FIGS. 9 to 11 comprises a reduction in thickness toward the peripheral edge of the optic portion, by virtue of the inclination of the anterior surface 338, 438, 538 of the haptic element in the proximal zone so that the axial thickness is at the minimum close to the peripheral edge.

In the variant of FIG. 9, the radial width of the inner slope 336 of the first tooth 335 is at least twice the length of the inner slope 336A of the second tooth.

In the variant of FIG. 10, the sharp ridges are at the intersection of the posterior surface of the proximal portion of the haptic element and the free end of the U-shaped grooves 436. In such a variant, there is one tooth or sharp ridge 435 on either side of a thin segment which separates the free edges of the successive grooves 436.

The variant of FIG. 11 comprises a network of teeth similar to that of the embodiments of FIGS. 1 to 8, but in which the anterior surface 538 of the haptic element in the proximal zone is inclined toward the peripheral edge of the optic, as in the variants of FIGS. 9 and 10.

Naturally, many modifications may be made to the exemplary embodiment described above without departing from the context of the invention.

The invention claimed is:

1. An intraocular lens configured for implantation in a capsular bag after ablation of a crystalline lens, comprising:
    a central optic portion having a posterior surface with a sharp ridge at a periphery of the optic portion; and
    a haptic portion comprising anteriorly angulated haptic elements arranged at the periphery of the optic portion for positioning the intraocular lens in the capsular bag, so that the sharp ridge includes portions of the periphery of the optic portion at a junction with the haptic elements; and
    a posterior face of the haptic elements comprising a proximal zone at a junction with the periphery of the optic portion, each of the proximal zones comprising at least one tooth extending over substantially a whole width of each haptic element, the at least one tooth having a sharp edge designed to indent a posterior capsule in order to limit migration of epithelial cells from the haptic elements to the optic portion.

2. The intraocular lens according to claim 1, wherein the proximal zone comprises a network of teeth including at least two parallel teeth.

3. The intraocular lens according to claim 2, wherein a groove between successive ones of the teeth of the network of teeth on each haptic element has a radial section in a shape of a U or of a V and in that the sharp edge of each of the teeth is defined at an intersection of a posterior surface of the corresponding haptic element and a free edge of the grooves.

4. The intraocular lens according to claim 2, wherein the teeth of each haptic element have different radial widths.

5. The intraocular lens according to claim 1, wherein the sharp edge of the at least one tooth of each haptic element is substantially in continuity with a curvature of a posterior surface of the corresponding haptic element.

6. The intraocular lens according to claim 1, wherein a radial section of the teeth of each haptic element has substantially the same configuration and dimensions.

7. The intraocular lens according to claim 1, wherein the sharp edge of the at least one tooth is defined at an intersection of an outer slope at an acute angle defined relative to a posterior surface of the haptic element and an inner slope substantially perpendicular to the posterior surface of the corresponding haptic element.

8. The intraocular lens according to claim 1, wherein a height of the at least one tooth is between 0.05 mm and 0.1 mm.

9. The intraocular lens according to claim 1, wherein the sharp edge of the at least one tooth is at an intersection of two slopes inclined in opposite directions at approximately 40° to 70°.

10. The intraocular lens according to claim 1, wherein the sharp edge of the at least one tooth protrudes slightly relative to a posterior surface of the corresponding haptic element.

11. The intraocular lens according to claim 1, wherein the at least one tooth comprises a slope inclined both posteriorly and toward the periphery of the optic portion.

12. The intraocular lens according to claim 1, wherein the at least one tooth extends over a radial width of 0.5 to 0.8 mm.

13. The intraocular lens according to claim 1, wherein each of the proximal zones is of generally triangular shape lying between the periphery of the optic portion and opposite edges of the corresponding haptic element.

14. The intraocular lens according to claim 1, wherein a posterior surface of each haptic element is slightly offset relative to the posterior surface of the optic portion by the height of the sharp ridge at a peripheral edge.

15. The intraocular lens according to claim 1, wherein the intraocular lens comprises a hydrophobic or hydrophilic flexible acrylic polymer.

16. An intraocular lens for implantation in a capsular bag after ablation of a crystalline lens, comprising
    a central optic portion having a posterior surface with a sharp ridge at a periphery of the optic portion; and
    a haptic portion comprising anteriorly angulated haptic elements arranged at the periphery of the optic portion for positioning the intraocular lens in the capsular bag; and
    a posterior face of the haptic elements comprising a proximal zone close to the periphery of the optic portion, each of the proximal zones comprising at least one tooth extending over substantially a whole width of each haptic element, the at least one tooth having a sharp edge designed to indent a posterior capsule to limit the migration of epithelial cells of the haptic elements toward the optic portion,
    wherein the sharp edge of the at least one tooth of each haptic element is substantially parallel to the sharp ridge of the periphery of the optic portion and lies on a spherical surface on which also lies the sharp ridge.

* * * * *